United States Patent
Sun et al.

(10) Patent No.: US 9,689,797 B2
(45) Date of Patent: Jun. 27, 2017

(54) MICROSCOPY IMAGING STRUCTURE WITH PHASE CONJUGATED MIRROR AND THE METHOD THEREOF

(71) Applicant: NATIONAL CENTRAL UNIVERSITY, Jhongli, Taoyuan (TW)

(72) Inventors: Ching-Cherng Sun, Taoyuan (TW); Yeh-Wei Yu, Taoyuan (TW); Che-Chu Lin, Taoyuan (TW); Szu-Yu Chen, Taoyuan (TW)

(73) Assignee: National Central University, Taoyuan (TW)

( * ) Notice: Subject to any disclaimer, the term of this patent is extended or adjusted under 35 U.S.C. 154(b) by 614 days.

(21) Appl. No.: 13/652,206

(22) Filed: Oct. 15, 2012

(65) Prior Publication Data
US 2014/0049631 A1 Feb. 20, 2014

(30) Foreign Application Priority Data
Aug. 16, 2012 (TW) .............................. 101129807 A (51) Int. Cl.
| H04N 7/18 | (2006.01) |
| G01N 21/45 | (2006.01) |
| G02B 21/00 | (2006.01) |
| G02B 21/08 | (2006.01) |
| G02B 21/14 | (2006.01) |
| G02B 21/16 | (2006.01) |
| G02B 21/36 | (2006.01) |
| A61B 5/00 | (2006.01) |

(52) U.S. Cl.
CPC .......... *G01N 21/45* (2013.01); *G02B 21/0056* (2013.01); *G02B 21/082* (2013.01); *G02B 21/14* (2013.01); *G02B 21/16* (2013.01); *G02B 21/365* (2013.01); *A61B 5/0059* (2013.01)

(58) Field of Classification Search
CPC .......................... A61B 5/0059; G02B 21/0056
USPC ............................................... 348/79; 359/70
See application file for complete search history.

(56) References Cited

U.S. PATENT DOCUMENTS

| 2011/0109962 A1* | 5/2011 | Cui et al. ....................... 359/385 |
| 2013/0033695 A1* | 2/2013 | Kong .................. F41H 13/0062 356/28 |
| 2014/0008525 A1* | 1/2014 | Simon et al. .................. 250/226 |

OTHER PUBLICATIONS

Mudry et al., "Isotropic Diffraction-Limited Focusing Using a Single Objective Lens", Nov. 12, 2010, Institut Fresnel.*

* cited by examiner

*Primary Examiner* — Nguyen Truong
(74) *Attorney, Agent, or Firm* — Juan Carlos A. Marquez; Marquez IP Law Office, PLLC (57) ABSTRACT

The present invention discloses a microscopy imaging structure with phase conjugated mirror and the method thereof. The afore-mentioned imaging structure produces a reverse focusing conjugated probe beam together with an original probe beam. These two probe beams meet at the focal point in the object body to be probed, and an interference pattern is produced. The interval between any two consecutive wave fronts in the interference pattern is then half of the wavelength of the original probe beam, and hence the vertical resolution of the image is improved. The present invention also applies a light modulator module on the probe beam to easily adjust the depth of the focal point of the probe beam and the phase conjugated reverse focusing probe beam in the object body. With the adoption of this invention, the size or position limitation of the target object is eliminated and the imaging resolution is also improved.

19 Claims, 15 Drawing Sheets

FIG. 14

MICROSCOPY IMAGING STRUCTURE WITH PHASE CONJUGATED MIRROR AND THE METHOD THEREOF

BACKGROUND OF THE INVENTION

1. Technical Field

The present invention relates to a microscopy imaging structure with inverse focus by a phase conjugated mirror and a microscopy imaging method using inverse focus by phase conjugation, and more particularly, to a microscopy imaging structure with inverse focus by a phase conjugated mirror and a microscopy imaging method using inverse focus by phase conjugation which are used for probing human tissues in the field of medical treatments.

2. Description of Related Art

Figure 1:
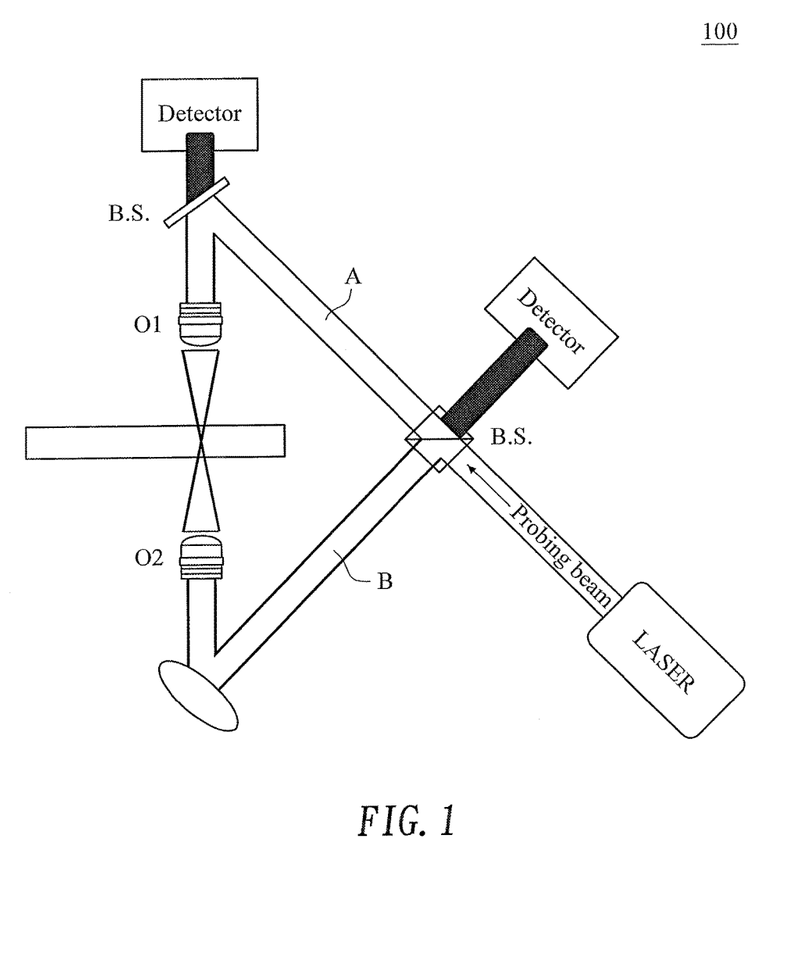
FIG. 1 is a diagram illustrating a prior art biomedical detection imaging structure.

FIG. 1 is a diagram illustrating a prior art biomedical detection imaging structure. This is a method commonly used for increasing the imaging resolution of biomedical tissue imaging apparatuses currently available. As shown in FIG. 1, the prior art biomedical detection imaging structure forms an image mainly by penetrating a probe beam through a biomedical tissue for the probing purpose or by exciting a phosphor which is injected into an object to be detected in advance.

At the right side of the diagram, a laser light source is used to provide a coherent beam, which is split into two probe beams (i.e., a probe beam A and a probe beam B) through a beam splitter. The probe beam A from the beam splitter is then focused by an objective lens O1 to a focal point in the object to be detected, and the probe beam B is reflected by a reflecting mirror to the other side of the object to be detected and is focused by the other objective lens O2 to the same focal point in the object to be detected. Signal lights are reflected and scattered by the object to be detected are respectively collected by the two objective lenses to two sensors for subsequent signal processing.

In practical applications, the method of FIG. 1 requires irradiation of probe beams from both sides of the object to be detected, and this indeed can also achieve the effect of collecting signals and forming an image. However, the most prominent problem with the method is that the thickness and shape of the object to be detected may seriously interfere the application of this method. Once the object to be detected has a volume too bulky, illuminating the probe beams from both sides of the object will become difficult and sometimes may even become impossible.

SUMMARY OF THE INVENTION

The present invention relates to a microscopy imaging structure with a phase conjugated mirror and a microscopy imaging method using phase conjugation. The microscopy imaging structure with a phase conjugated mirror comprises a first beam splitter, an objective lens and a phase conjugated mirror. The primary objective of the present invention is to achieve detection of a biomedical tissue from only one side of the object and to increase the longitudinal resolution of microscopy imaging.

To achieve the aforesaid objective, the present invention provides a microscopy imaging structure with a phase conjugated mirror, which comprises: a first beam splitter, having a first input end, a first light guide end and a first output end; an object lens, being disposed in a light path of the first light guide end; and a phase conjugated module, being disposed in a light path of the first output end.

To achieve the aforesaid objective, the present invention further provides a microscopy imaging method using phase conjugation, which comprises the following steps: focusing a probe beam into a biomedical tissue by means of an objective lens; using the objective lens to collect the light is scattered and reflected from the biomedical tissue for use as a signal light; utilizing the phase conjugation mirror (PCM) to obtain a conjugated signal light; and introducing the original signal light and adjusting a light intensity of the original signal light so as to form the high resolution interference patterns with the conjugated signal light.

With the embodiment of the present invention can at least achieve the following inventive progress:

I. the longitudinal resolution of microscopy imaging can be increased multiple times by applying a probe beam from only one side of the object;

II. Scattering of signal light can be reduced to increase the biomedical imaging efficiency;

III. High resolution microscopy imaging can be achieved without being limited by the thickness of the biomedical tissue to be detected; and IV. The focusing position of the probe beam can be adjusted according to the application requirements so that the probe beam can approach deeper positions in the biomedical tissue to be detected.

The above description is only a summary of the technical solution of the present invention. In order to shed more light on the technical means of the present invention, a detailed description of the preferred embodiments is provided below with reference to the accompanying drawings so that a person skilled in the art can easily understand the above and other objects, as well as the characteristics and advantages, of the present invention and implement the present invention according to the contents disclosed herein.

DETAILED DESCRIPTION OF THE EMBODIMENTS OF THE INVENTION

To further demonstrate the technical means adopted by the present invention to achieve the intended objects and the effects of such technical means, a detailed description of the best mode of carrying out the invention, as well as the structure, characteristics, and functions of the disclosed flexible backlight module, is given below with reference to the drawings and the preferred embodiments.

The above and other technical contents, features, and effects of the present invention are clearly presented in the detailed description of the preferred embodiments and the accompanying drawings. For the convenience of description, the same components in the following embodiments are indicated by the same reference numerals.

First Embodiment

Figure 2:
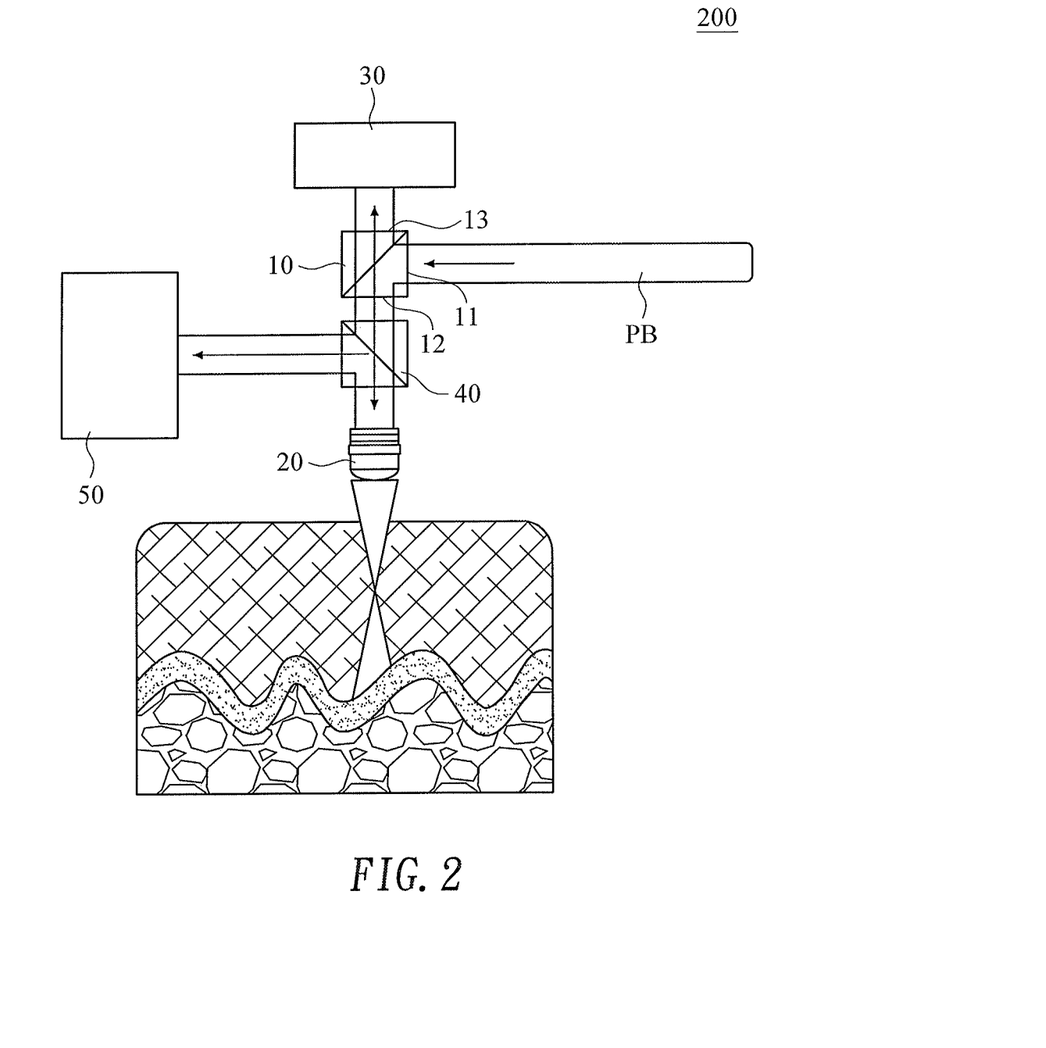
FIG. 2 is a perspective view of a microscopy imaging structure with a phase conjugated mirror according to an embodiment of the present invention.

As shown in FIG. 2, an embodiment of a microscopy imaging structure 200 with a phase conjugated mirror of the present invention comprises a first beam splitter 10, an objective lens 20 and a phase conjugated mirror 30.

The first beam splitter 10 has a first input end 11, a first light guide end 12 and a first output end 13. Firstly, a coherent laser beam is input through the first input end 11 as a probe beam PB, which is then output to an objective lens through the first light guide end 12. Then, a signal light is received by the objective lens through the first light guide end 12 again. Finally, the received signal light is output to the phase conjugated mirror 30 through the first output end 13.

The objective lens 20 is disposed in a light path of the first light guide end 12. The objective lens firstly receives the probe beam PB output from the first light guide end for projection into an object, such as a human tissue, to be detected, and then receives the signal light reflected from the object to be detected for output to the first light guide end 12.

The phase conjugated mirror 30 is disposed in a light path of the first output end 13. The phase conjugated mirror 30 may be a phase conjugated mirror or a phase conjugated signal processing module.

A second beam splitter 40 may be further disposed in a light path of the reflected light received by the objective lens 20. The second beam splitter 40 is adapted to guide the signal light to the first light guide end 12 and an image detecting system 50 disposed in an output light path of the second beam splitter 40.

The image detecting system 50 is to capture the image data of the biomedical tissue to be detected and to carry out necessary supervision, observation or early image display requirements.

Second Embodiment

Figure 3:
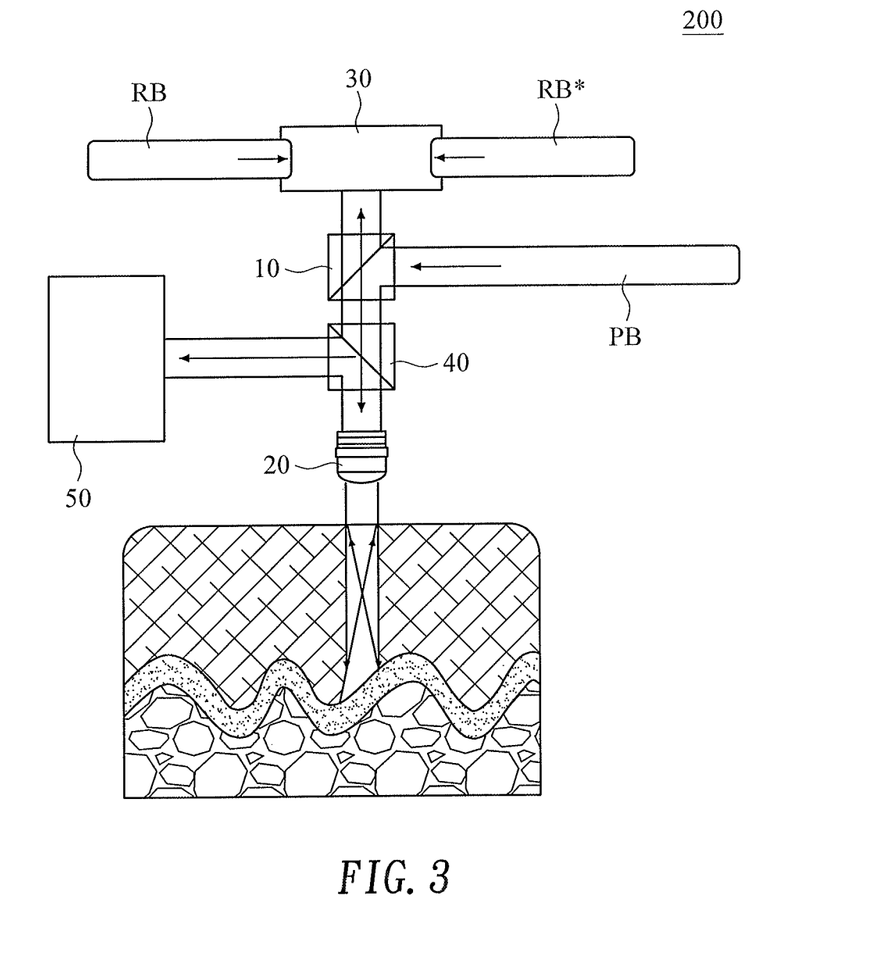
FIG. 3 is an example of generating a conjugated probe beam.

As shown in FIG. 3, this embodiment is mainly configured according to the first embodiment, with the phase conjugated module 30 of this embodiment being a phase conjugated mirror 30.

The phase conjugated mirror is commonly used in the filed of imaging technologies. The recording medium of the phase conjugated mirror mostly lithium niobate crystals, barium titanate crystals, and photorefractive crystals and so on. When a reference beam RB is introduced to generate interference with the signal light in the phase conjugated mirror, interference patterns can be recorded by the crystals of the phase conjugated mirror.

When a conjugated reference beam RB* is introduced into the crystals, a conjugated signal light will be diffracted by the crystal. The conjugated signal light is then projected into the biomedical tissue by the objective lens to generate a conjugated probe beam PB* which is focused in the reverse direction of the probe beam PB.

For the interference patterns generated by the probe beam PB and the conjugated probe beam PB* reflected from the biomedical tissue to be detected, the spacing there between is reduced to half of the wavelength of the original probe beam. Therefore, through embodiment of the present invention, the longitudinal resolution of microscopy imaging can be increased through irradiation of probe beams from one single direction.

Third Embodiment

Figure 4:
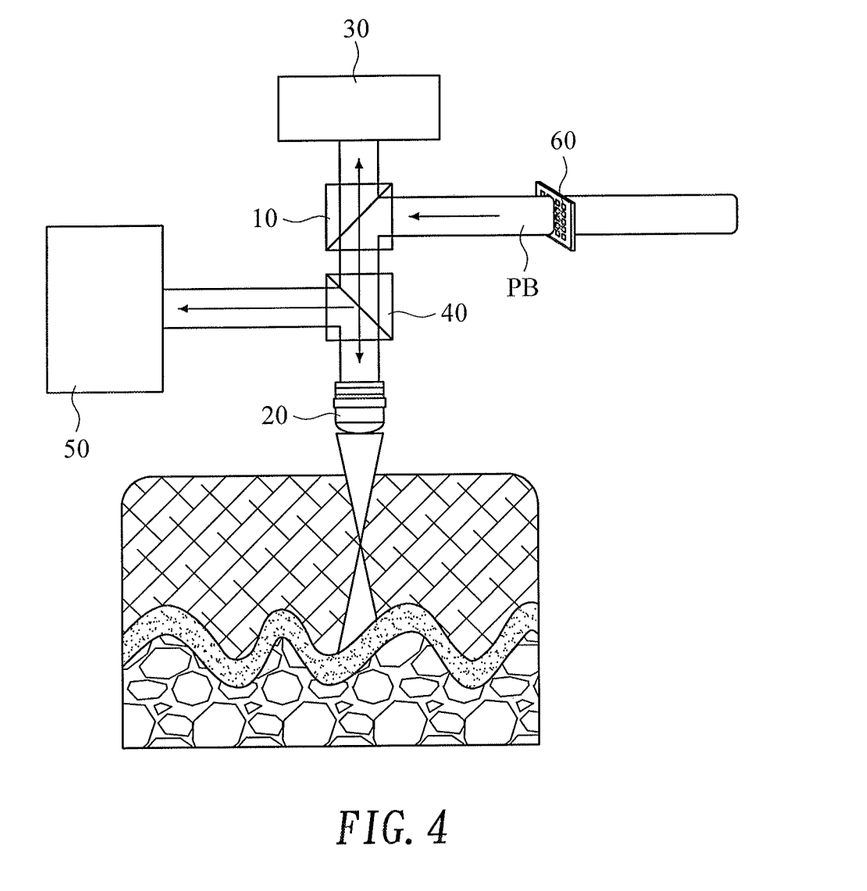
FIG. 4 is a perspective view of an embodiment of the present invention adopting a spatial light modulator.

As shown in FIG. 4, in the embodiments of the first and the second embodiments, a spatial light modulator 60 may further be introduced in the light path of the first input end 11. The spatial light modulator 60 is adapted to modulate the initial phases of the probe beam to reduce scattering of the biomedical tissue to be detected so that the probe beam can be focused to a deeper position and the energy is more concentrated. This also increases the efficiency of microscopy imaging of the biomedical tissue.

Fourth Embodiment

Figure 5:
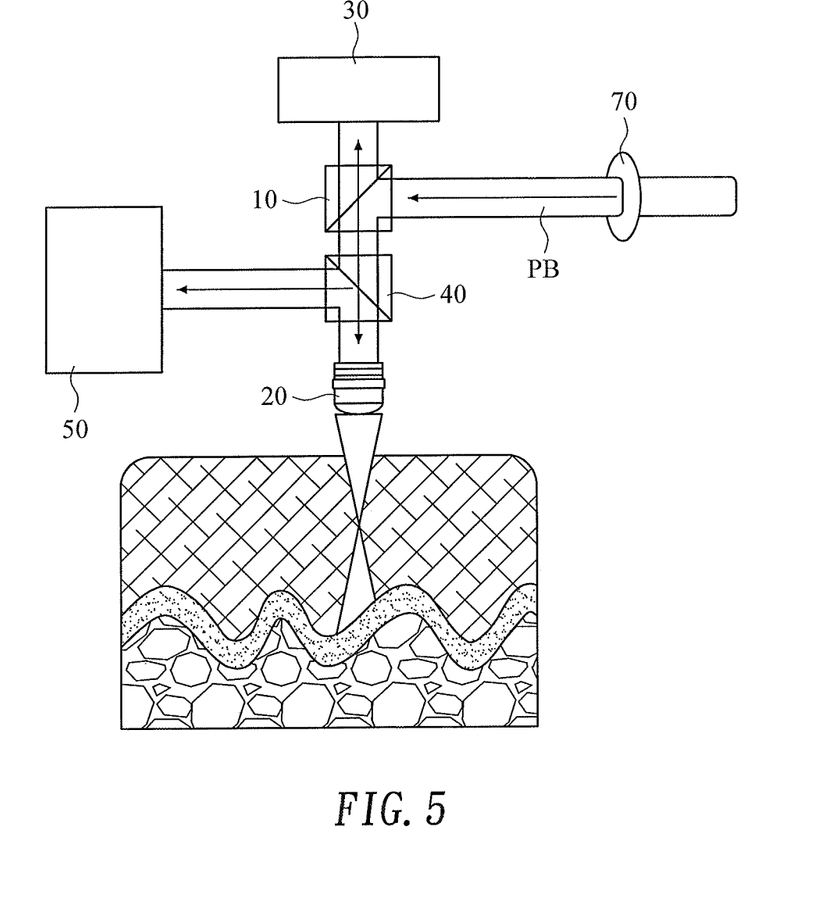
FIG. 5 is a perspective view of an embodiment of the present invention adopting an attenuator.

As shown in FIG. 5, in the embodiments of the first and the second embodiments, an attenuator 70 may also be disposed in the light path of the first input end 11. While the conjugated probe beam PB* that is focused in the reverse direction is generated, an original probe beam PB is input from the first input end 11 and a light intensity of the original probe beam PB is adjusted by the attenuator 70 to be equal to the light intensity of the conjugated signal light diffracted. By means of this composition, high resolution interference patterns are generated by the two oppositely focused beams to increase the clearance of the imaging.

Fifth Embodiment

Figure 6:
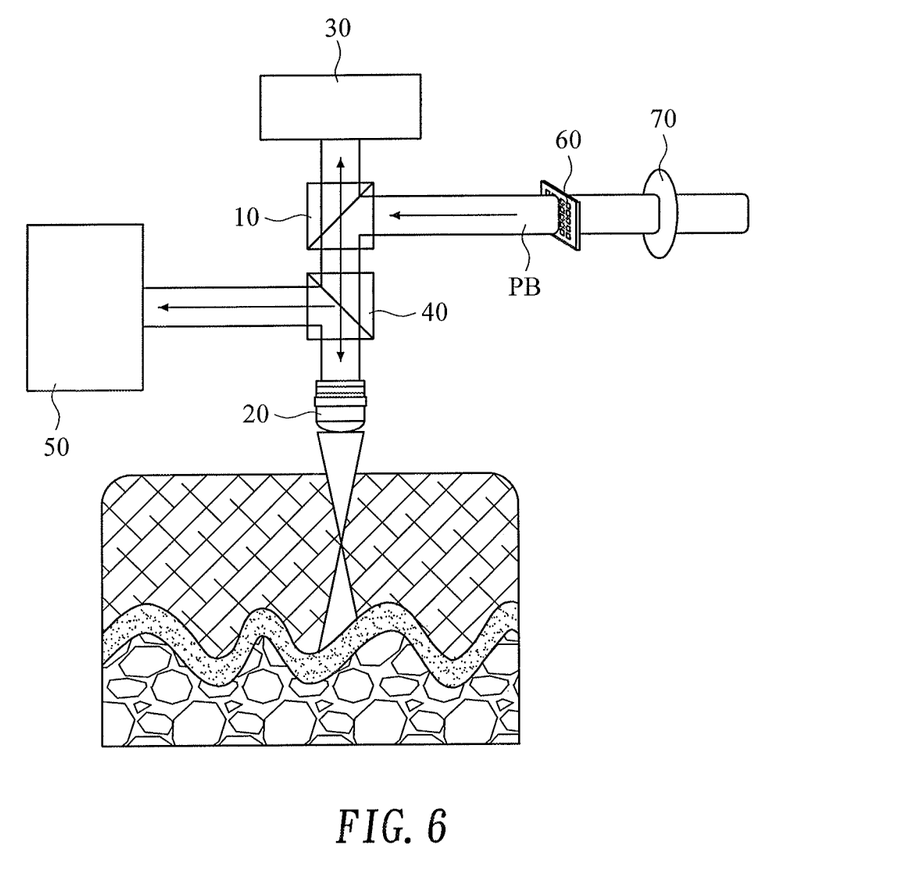
FIG. 6 is a perspective view of an embodiment of the present invention adopting a spatial light modulator and an attenuator.

As shown in FIG. 6, in the embodiments of the first and the second embodiments, a spatial light modulator 60 and an attenuator 70 may be disposed in the light path of the first input end 11, and this can simultaneously achieve multiple advantages: clear images can be formed, deeper tissues can be detected and the imaging efficiency can be increased. This structure can achieve the same effect as delivered by two opposite beams of the 4pi microscope simply by applying a probe beam from one side of the biomedical tissue, and can be particularly applied to optical tweezers and photodynamic therapy in medical surgery.

Sixth Embodiment

Figure 7:
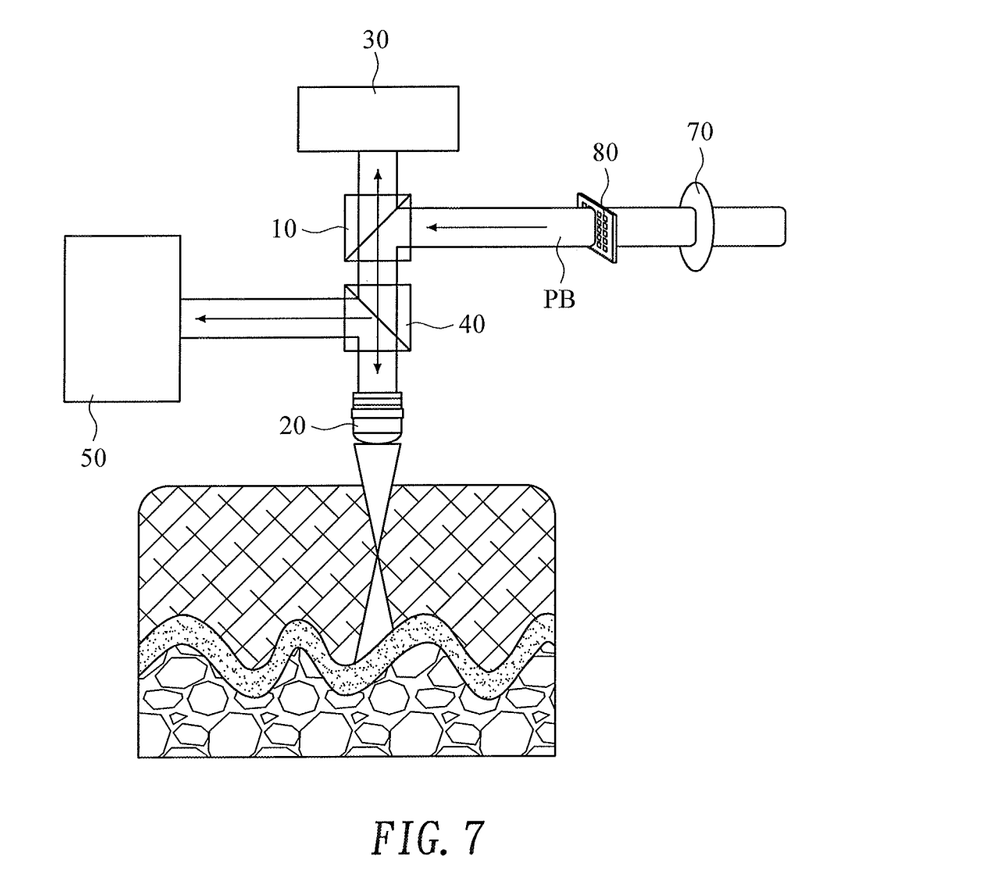
FIG. 7 is a perspective view of an embodiment of the present invention adopting a electro-light modulator and an attenuator.

As shown in FIG. 7, in the embodiments of the fourth embodiments, an electro-optic modulator 80 may be disposed in the light path of the first input end 11. The electro-optic modulator 80 is adapted to modulate the phase of the probe beam to change positions of bright fringes of the interference patterns and to depleted the spontaneous fluorescent light particles around an observation point in the biomedical tissue so that a better longitudinal resolution of imaging can be achieved. This can be applied to the combination of the 4pi microscopy and the STED (Stimulated Emission Depletion) microscopy.

Seventh Embodiment

Figure 8:
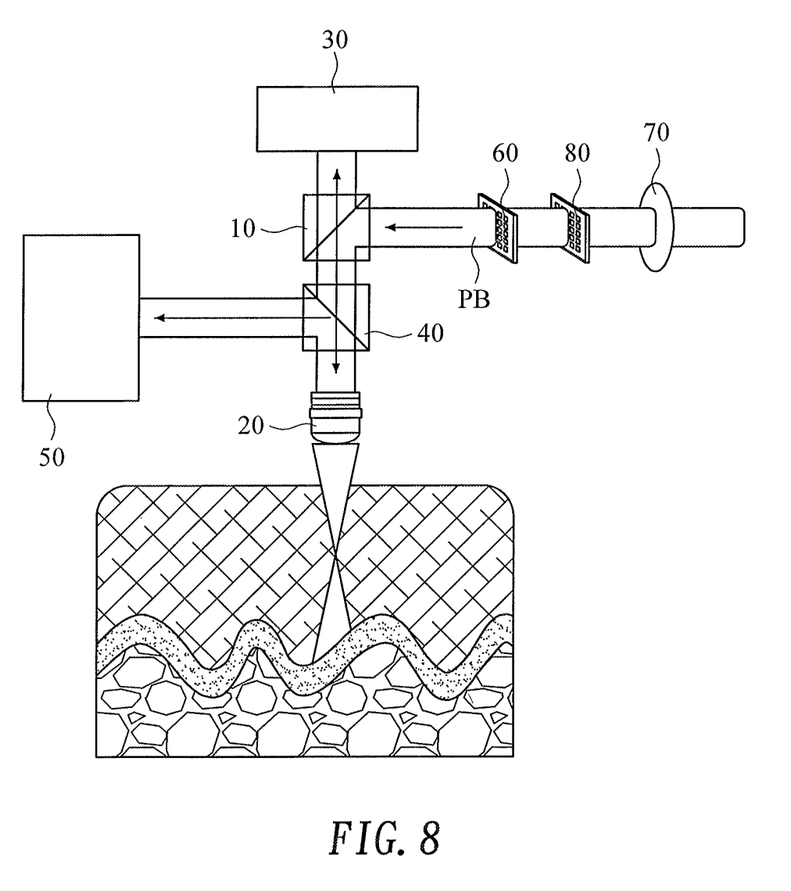
FIG. 8 is a perspective view of an embodiment of the present invention adopting a spatial light modulator, an electro-light modulator, and an attenuator.

As shown in FIG. 8, in the embodiments of the first and the second embodiments, a spatial light modulator 60, an electro-optic modulator 80 and an attenuator 70 may be disposed in the light path of the first input end 11. The purpose of this is to combine the functions of the three components together to achieve the advantages such as increasing the resolution, obtaining bright interference patterns and focusing the probe beam to deeper tissues.

Eighth Embodiment

Figure 9:
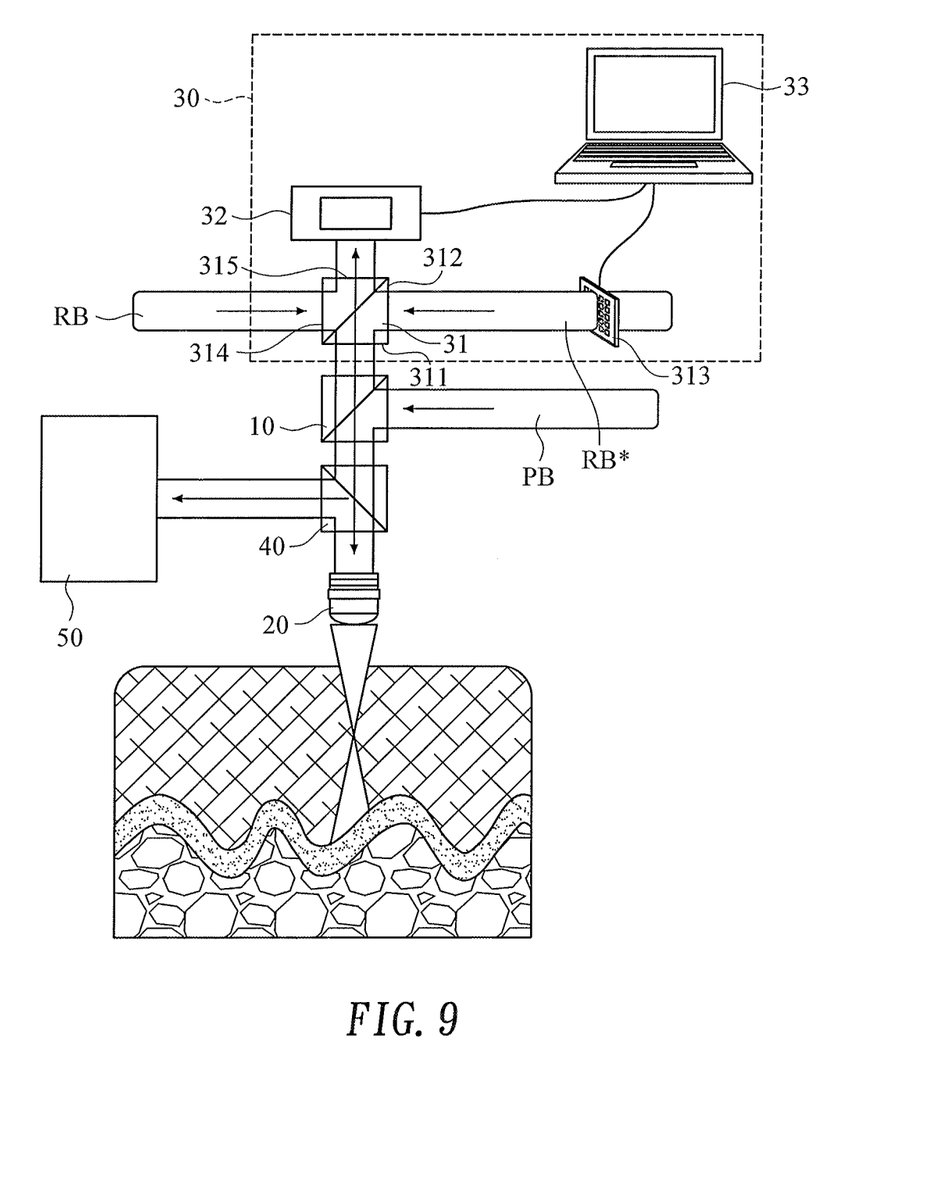
FIG. 9 is a perspective view of an embodiment of the present invention adopting a digital holographic phase conjugated mirror.

As shown in FIG. 9, the phase conjugated mirror of each of the second to the seventh embodiments can be replaced with a digital holographic phase conjugated mirror 30. The digital holographic phase conjugated mirror 30 in this embodiment comprises a third beam splitter 31, an image sensor 32 and a light signal processing system 33.

The third beam splitter 31 has: a second light guide end 311 coupled to the first output end 13; a second input end 312, wherein a spatial light modulator 313 is disposed in an input light path of the second input end 312; a third input end 314; and a second output end 315.

The image sensor is disposed in a light path of the second output end 315. The image sensor is adapted to detect the signal light reflected from the biomedical tissue and the conjugated signal light and to record and output corresponding electronic signals. The light signal processing system, which is a processor circuit system, is adapted to output a control signal to the spatial light modulator 313 and read an output signal of the image sensor for imaging or for other control applications required.

Ninth Embodiment

Figure 10:
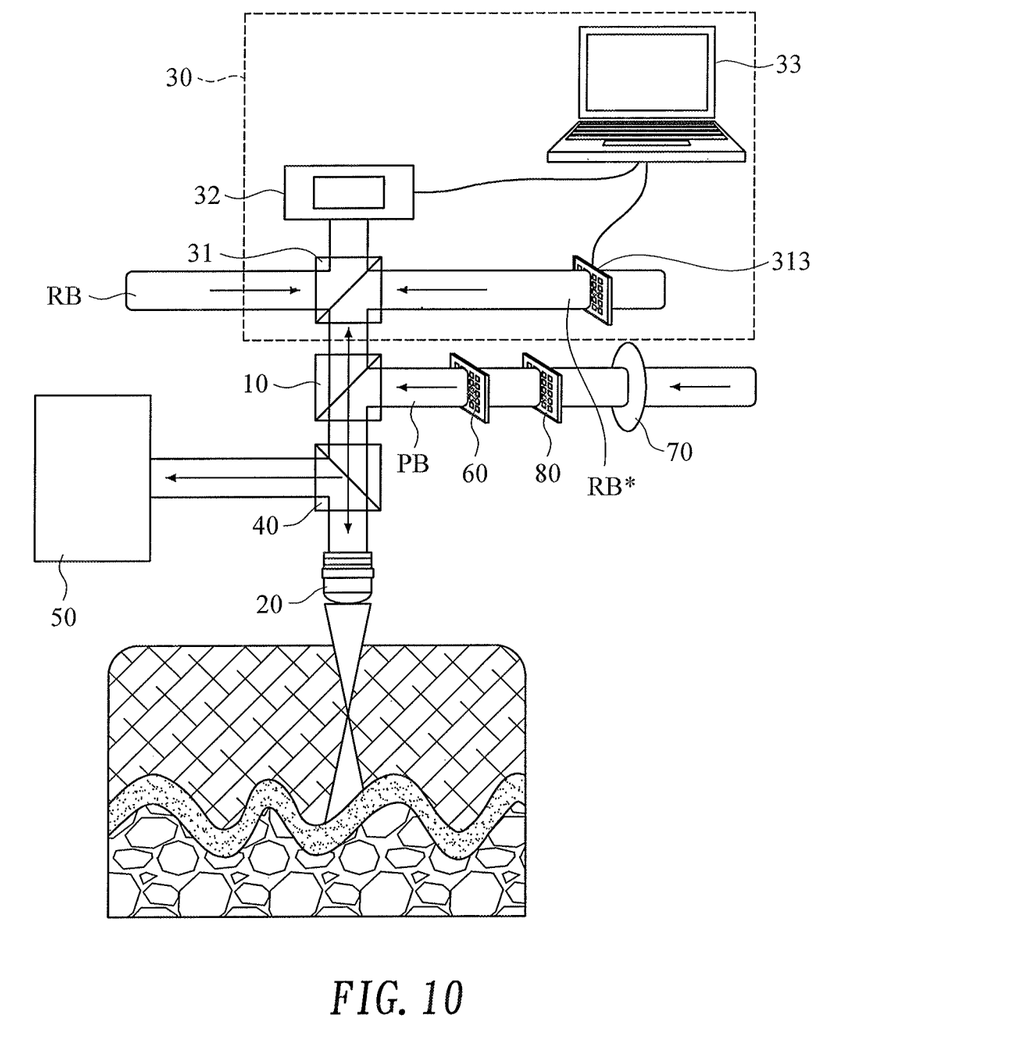
FIG. 10 is a perspective view of an embodiment of the present invention adding a spatial light modulator, an electro-light modulator, and an attenuator to the embodiment in FIG. 9.

As shown in FIG. 10, in the eighth embodiment described above, a spatial light modulator 60, an electro-optic modulator 80 and an attenuator 70 may further be cascaded in the light path of the first input end 11 so that the functions of the three components can be combined together to achieve the advantages such as increasing the resolution, obtaining bright interference patterns and focusing the probe beam to deeper tissues.

Tenth Embodiment

Figure 11A:
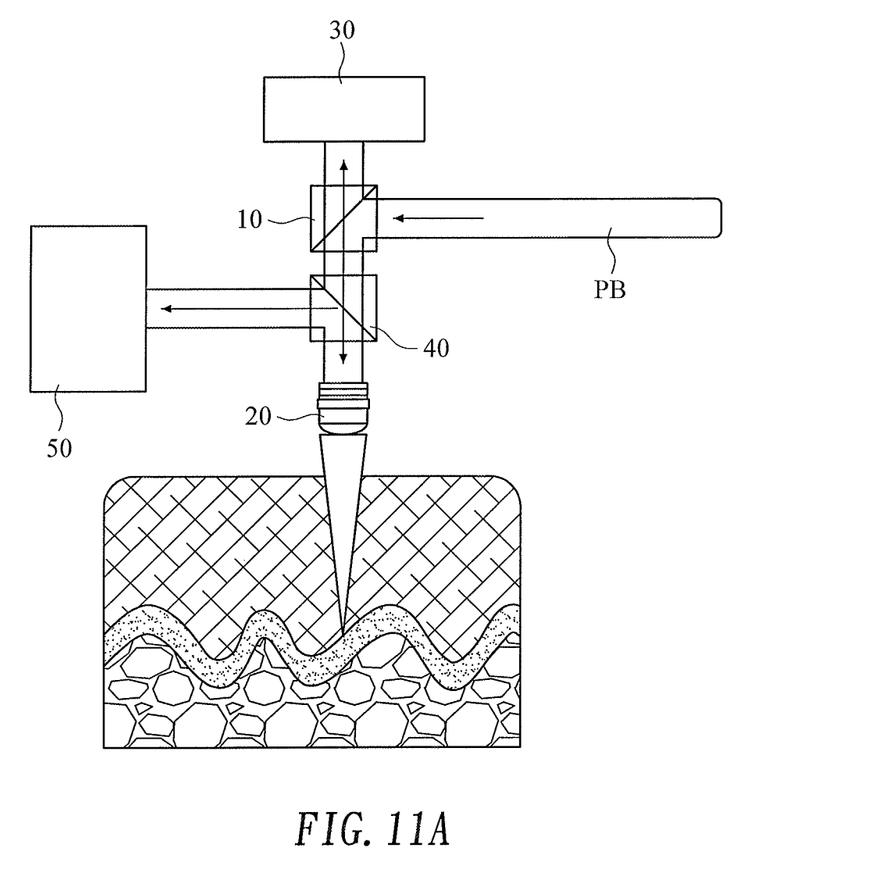
FIG. 11A is a perspective view of an embodiment of the present invention.
Figure 11B:
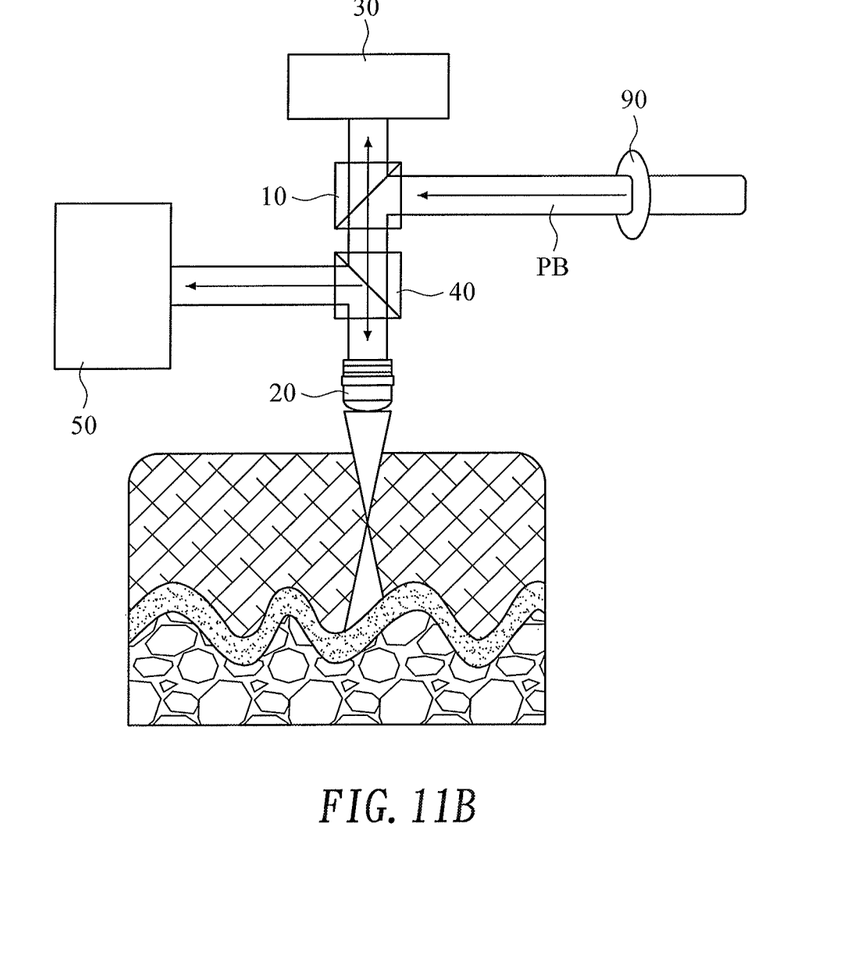
FIG. 11B is a perspective view of an embodiment of adding a lens to the embodiment in FIG. 11A.

As shown in FIG. 11B, in the embodiments of the first and the second embodiments, a lens 90 may further be disposed in the light path of the first input end 11. In one embodiment of the present invention, the lens 90 can adjust the position and the depth at which the probe beam PB is focused so that the probe beam PB can be focused at any position in the biomedical tissue to be detected, together with the adjustment of the objective lens 20 to focus on the brighter spot, the recording efficiency is promoted, which makes the applications wider.

Figure 13:
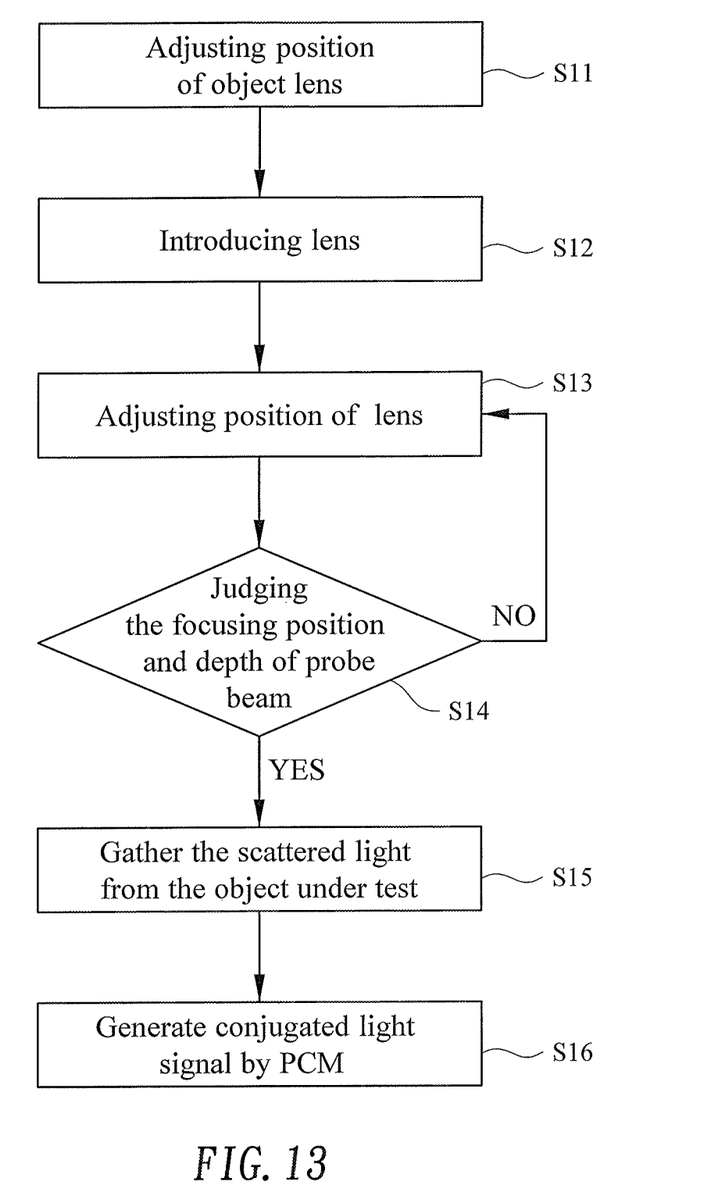
FIG. 13 is a flow chat of the embodiment in FIG. 11B.

As shown in FIG. 13 is a flowchart diagram of the tenth embodiment. Firstly, adjusting position of objective lens (S11) so that the laser beam is focused to an interface of the biomedical tissue and the reflected light at the interface is received by the objective lens 20 (as shown in FIG. 11A). Then, introducing lens (S12) and adjusting position of lens (S13), and then judging the focusing position and depth of probe beam (S14). As also shown in FIG. 11B, when the probe beam reaches the desired focus point and the desired focus depth, the objective lens 20 is used to gather the scattered light from the object under test (S15) for use as a signal light. Finally, the phase conjugation mirror (PCM) is utilized to obtain a conjugated signal light: generate conjugated light signal by PCM (S16), which is a focused light emitted from inside of the biomedical tissue. The reversely focusing efficacy of the present invention can not only allow the objective lens 20 to receive reflected lights from wider part of the object tissue to further increase the recording efficiency of this system, but also be applied to varieties of non-linear optical microscopy, such as duplication microscopy, triplication microscopy and multi-photon fluorescence microscopy.

Figure 12:
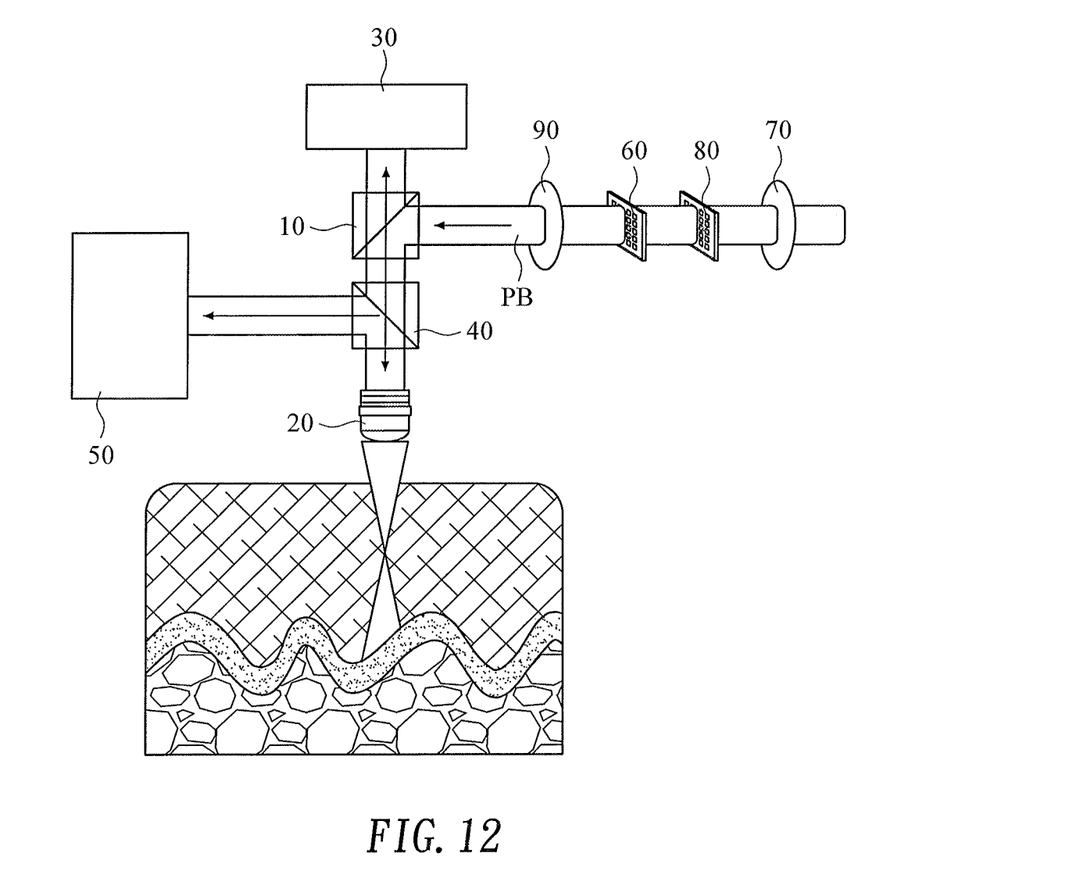
FIG. 12 is a perspective view of an embodiment of the present invention adopting a spatial light modulator, an electro-light modulator, an attenuator, and a lens.

With the function of adjusting the focus position of the probe beam PB of the lens 90 may further be additionally disposed in the light path of the first input end 11 of each of the third to the ninth embodiments to make the application of the present invention more flexible. FIG. 12 shows a diagram illustrating an embodiment of introducing a lens 90 to the imaging structure of the seventh embodiment.

<Microscopy Imaging Method Using Phase Conjugation>

Figure 14:
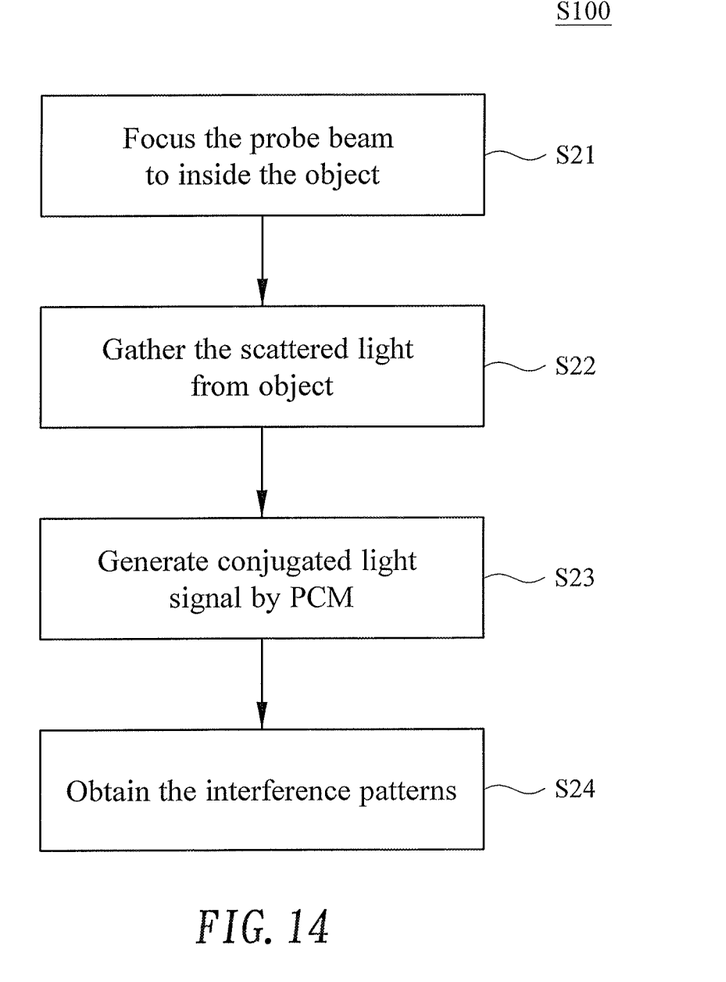
FIG. 14 illustrates an embodiment of a microscopy imaging method using phase conjugation of the present invention.

As shown in FIG. 14, there is shown a microscopy imaging method S100 using phase conjugation of the present invention, which comprises the following steps of: focus the probe beam to inside the object (step S21), the object can be a biomedical tissue; gather the scattered light from the object (step S22); generate conjugated light signal by PCM (step S23); and introducing the original signal light and adjusting a light intensity of the original signal light so as to obtain the interference patterns (step S24), that is, to form high resolution interference patterns with the conjugated signal light.

The step S21 of "focus the probe beam to inside the object" is carried out by using the objective lens 20 to focus the probe beam PB into the object biomedical tissue.

The step S22 of "gather the scattered light from the object" is carried out by using the objective lens 20 to collect the light rays scattered and reflected from the object biomedical tissue for use as a signal light received.

The step S23 of "generate conjugated light signal by PCM" is carried out by utilizing the PCM of the present invention to obtain the conjugated signal light which is conjugated in phase with the original signal light. The conjugated signal light has the function of a focused light emitted from the inside of the object biomedical tissue.

The step S24 of "obtain the interference patterns" is introducing the original signal light and adjusting the intensity of the original signal light so as to form high resolution interference patterns with the conjugated signal light.

Through execution of the above steps, high resolution interference patterns are formed by the microscopy imaging method S100 using phase conjugation of the present invention. This high-resolution interference patterns can be used in optical tweezers and photodynamic therapy of medical treatment instruments, and can achieve the high definition and the high resolution of the 4pi microscope.

The embodiments described above are only the preferred embodiments of, but not limitations to, the present invention. While the present invention is disclosed herein with reference to the preferred embodiments, the embodiments are not intended to restrict the present invention. Based on the technical contents disclosed herein, a person skilled in the art may alter or modify the foregoing embodiments and thereby produce equivalent embodiments without departing from the scope of the present invention. Therefore, all minor alterations and equivalent changes which are based on the technical substance of the present invention and made to the foregoing embodiments should be considered as within the scope of the technical solution of the present invention.

What is claimed is:

1. A microscopy imaging structure with a phase conjugated mirror configured for use with biomedical tissue that is opaque so as to prevent projecting light therethrough, comprising:
    a first beam splitter, having a first input end, a first light guide end and a first output end;
    an objective lens, being disposed in a light path of the first light guide end;
    a phase conjugated mirror, being disposed in a light path of the first output end; and
    a conjugated probe beam, being generated from inside the biomedical tissue that is opaque to light projecting therethrough in a light path of the first light guide end and projected from the said biomedical tissue through the objective lens to the first light guide end, wherein the conjugated probe beam is configured as a focused light emitted from inside of the biomedical tissue such that the biomedical tissue appears illuminated by a conjugated light projecting from behind the biomedical tissue.

2. The microscopy imaging structure of claim 1, wherein a spatial light modulator is further disposed in a light path of the first input end.

3. The microscopy imaging structure of claim 1, wherein an attenuator is further disposed in the light path of the first input end.

4. The microscopy imaging structure of claim 1, wherein a lens is further disposed in the light path of the first input end.

5. The microscopy imaging structure of claim 1, wherein a spatial light modulator and an attenuator are further cascaded in the light path of the first input end.

6. The microscopy imaging structure of claim 1, wherein an electro-optic modulator and an attenuator are further cascaded in the light path of the first input end.

7. The microscopy imaging structure of claim 1, wherein a spatial light modulator, an electro-optic modulator and an attenuator are further cascaded in the light path of the first input end.

8. The microscopy imaging structure of claim 1, wherein a spatial light modulator, an electro-optic modulator, an attenuator and a lens are further cascaded in the light path of the first input end.

9. The microscopy imaging structure of claim 1, wherein a second beam splitter is further disposed in a light path of reflected light received by the objective lens, and an image detecting system is disposed in an output light path of the second beam splitter.

10. The microscopy imaging structure of claim 9, wherein the phase conjugated module comprises:
    a third beam splitter, having: a second light guide end coupled to the first output end; a second input end, wherein a spatial light modulator is disposed in an input light path of the second input end; a third input end; and a second output end;
    an image sensor, being disposed in a light path of the second output end; and
    a light signal processing system, being adapted to output a control signal to the spatial light modulator and read an output signal of the image sensor.

11. The microscopy imaging structure of claim 10, wherein a spatial light modulator, an electro-optic modulator and an attenuator are further cascaded in the light path of the first input end.

12. A microscopy imaging method using phase conjugation for use with biomedical tissue that is opaque so as to prevent projecting light therethrough, comprising the steps of:
    focusing a probe beam to inside biomedical tissue;
    gathering the scattered light from the biomedical tissue;
    generating conjugated light signal by PCM; and
    obtaining the interference patterns, which is carried out by introducing the original signal light and adjusting the light intensity thereof to form the high resolution interference patterns with the conjugated signal light, wherein the conjugated signal light is emitted from inside of the biomedical tissue that is opaque to light projecting therethrough such that the biomedical tissue appears illuminated by a conjugated light projecting from behind the biomedical tissue.

13. The microscopy imaging structure of claim 2, wherein a second beam splitter is further disposed in a light path of reflected light received by the objective lens, and an image detecting system is disposed in an output light path of the second beam splitter.

14. The microscopy imaging structure of claim 3, wherein a second beam splitter is further disposed in a light path of reflected light received by the objective lens, and an image detecting system is disposed in an output light path of the second beam splitter.

15. The microscopy imaging structure of claim 4, wherein a second beam splitter is further disposed in a light path of reflected light received by the objective lens, and an image detecting system is disposed in an output light path of the second beam splitter.

16. The microscopy imaging structure of claim 5, wherein a second beam splitter is further disposed in a light path of reflected light received by the objective lens, and an image detecting system is disposed in an output light path of the second beam splitter.

17. The microscopy imaging structure of claim 6, wherein a second beam splitter is further disposed in a light path of reflected light received by the objective lens, and an image detecting system is disposed in an output light path of the second beam splitter.

18. The microscopy imaging structure of claim 7, wherein a second beam splitter is further disposed in a light path of reflected light received by the objective lens, and an image detecting system is disposed in an output light path of the second beam splitter.

19. The microscopy imaging structure of claim 8, wherein a second beam splitter is further disposed in a light path of reflected light received by the objective lens, and an image detecting system is disposed in an output light path of the second beam splitter.

* * * * *